United States Patent [19]

Acker et al.

[11] 4,395,555

[45] Jul. 26, 1983

[54] PREPARATION OF 2-AMINOPYRIDINE DERIVATIVES

[75] Inventors: Rolf-Dieter Acker, Leimen; Gerhard Hamprecht, Weinheim, both of Fed. Rep. of Germany

[73] Assignee: BASF Aktiengesellschaft, Fed. Rep. of Germany

[21] Appl. No.: 338,112

[22] Filed: Jan. 8, 1982

[30] Foreign Application Priority Data

Jan. 30, 1981 [DE] Fed. Rep. of Germany ....... 3103065

[51] Int. Cl.$^3$ .................. C07D 213/55; C07D 213/57
[52] U.S. Cl. ..................................... 546/289; 546/318
[58] Field of Search ............................... 546/318, 289

[56] References Cited

U.S. PATENT DOCUMENTS 3,974,159  8/1976  Decker et al. ...................... 544/177

FOREIGN PATENT DOCUMENTS 1811973  6/1970  Fed. Rep. of Germany ...... 546/288

OTHER PUBLICATIONS

Ege et al., Synthesis, (1979), pp. 376–378, Verlag publishers.
Ullmanns Encyklopädie der technischen Chemie, vol. 8, p. 503, (1957).
Ullmanns Encyklopädie der technischen Chemie, vol. 14, p. 480, (1963).
Ullmanns Encyklopädie der technischen Chemie, vol. 18, pp. 195–198, (1967).

*Primary Examiner*—Alan L. Rotman
*Attorney, Agent, or Firm*—Keil & Witherspoon

[57] ABSTRACT

2-Aminopyridine derivatives are prepared by reacting a quaternary ammonium compound with malodinitrile in the presence of an alkanol, followed by reaction with ammonia in the presence of an alkanol, water and/or an ether to give aminonicotinonitrile and, if desired, then reacting this product with an alkali metal compound to give aminonicotinic acid.

The 2-aminopyridine derivatives obtainable by the process of the invention are valuable starting materials for the preparation of pesticides, drugs, vitamins and dyes.

10 Claims, No Drawings

PREPARATION OF 2-AMINOPYRIDINE DERIVATIVES

The present invention relates to a process for the preparation of 2-aminopyridine derivatives by reacting a quaternary ammonium compound with malodinitrile in the presence of an alkanol, followed by reaction with ammonia in the presence of an alkanol, water and/or an ether to give aminonicotinonitrile and, if desired, then reacting this product with an alkali metal compound to give aminonicotinic acid.

The preparation of quaternary ammonium compounds, which are also derivatives of malonaldehyde, of the formula

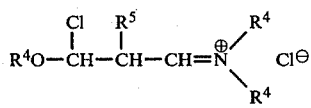

where $R^4$ is alkyl and $R^5$ is alkyl or H, by reacting phosgene with a dialkylformamide to give a dialkylformamidechloride and then reacting the product with an enol ether has been disclosed (German Laid-Open Application DOS 2,424,373).

Furthermore, it is known (Synthesis 1979, pages 376 to 378) that alkylidene malodinitriles can be reacted with lithium-diisopropylamide in tetrahydrofuran at $-65°$ C. and the product then reacted with dimethylformamide dichloride to give 4-dimethylamino-1,3-butadiene-1,1-dicarbonitriles. These butadiene compounds can be converted to 2-aminopyridines by reaction with ammonia in methanol.

In a similar manner, as described in German Laid-Open Application DOS 1,811,973, 2-amino-5,6-dihydro-4-methylthiobenzoquinoline-3-carbonitrile is obtained by reacting 2-methylthio-2-(3,4-dihydro-1-pyrrolidino-2-naphthyl)-ethylene-1,1-dicarbonitrile with aqueous ammonia in the presence of methanol.

We have found that 2-aminopyridine derivatives of the formula

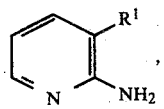

where $R^1$ is cyano or carboxyl, are advantageously obtained if a quaternary ammonium compound of the formula

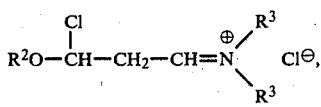

where the individual radicals $R^2$ and $R^3$ can be identical or different and each is an aliphatic radical, (a) is reacted with malodinitrile in the presence of an alkanol,
(b) the resulting reaction mixture is then reacted with ammonia in the presence of an alkanol, water and/or an ether and, if desired,
(c) the aminonicotinonitrile thus obtained is reacted with an alkali metal compound.

If N,N-(3-chloro-3-ethoxypropylidene)-N,N-dimethylammonium chloride is used, the reaction can be represented by the following equation:

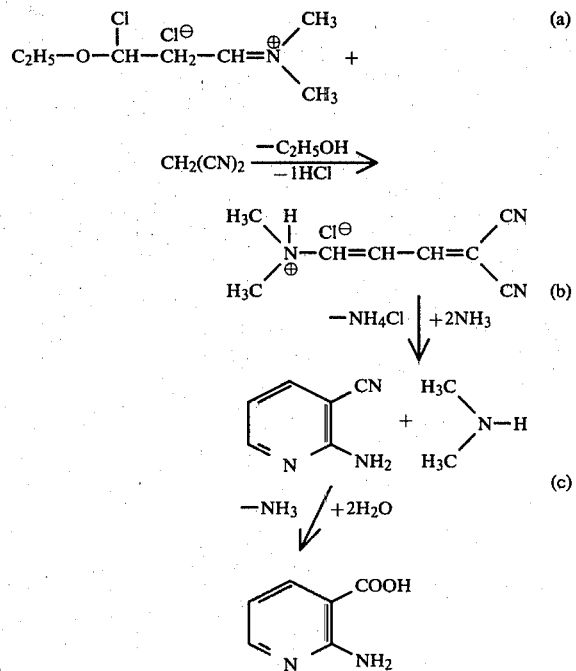

Compared to the known processes, the process according to the invention gives aminonicotinic acid and its nitrile by a simpler and more economical route, in good yield and purity and with a better overall space/time yield. Reactants, such as lithium compounds, which are difficult to obtain are avoided. Both the nitrile and the acid can be prepared in a one-vessel process, without isolating the intermediates. All these advantageous results are surprising in view of the prior art.

The starting material II is readily prepared by the process described in German Laid-Open Application DOS. No. 2,424,373, and can be reacted with the malodinitrile in the stoichiometric amount or in excess, advantageously using from 0.5 to 3.0, preferably from 0.5 to 1.5, moles of malodinitrile per mole of starting material II. Preferred starting materials II and, correspondingly, preferred end products I are those in whose formulae $R^2$ and $R^3$ are identical or different and each is alkyl of 1 to 7, preferably of 1 to 4, carbon atoms, particularly methyl or ethyl, and $R^1$ is cyano or carboxy. The above radicals can also be substituted by groups which are inert under the reaction conditions, e.g. alkyl or alkoxy of 1 to 4 carbon atoms.

Thus, examples of suitable starting materials II and N,N-(3-chloro-3-ethoxypropylidene)-N,N-dimethylammonium chloride; the homologous N,N-diethyl, N,N-dipropyl, N,N-diisopropyl, N,N-dibutyl, N,N-diisobutyl, N,N-di-sec.-butyl and N,N-di-tert.-butyl derivatives; and the corresponding 3-methoxy, 3-propoxy, 3-isopropoxy, 3-butoxy, 3-isobutoxy, 3-sec-butoxy and 3-tert.-butoxy derivatives.

The alkanols used in (a) and (b) are advantageously identical and can be of 1-10, in particular 1-6, carbon atoms. Examples of suitable alkanols are methyl, ethyl, propyl, isopropyl, butyl, isobutyl, sec-butyl, and tert.-butyl alcohol, the first-mentioned being preferred. It is advantageous to use from 1 to 1,000, in particular from 10 to 100, moles of alkanol per mole of starting material II. The total quantity of alkanol can be employed in stage (a) or a portion, advantageously from 20 to 80 percent by weight, of the total quantity of alkanol can be added in stage (a) and the remaining portion in stage (b). Ammonia can be gaseous or liquid, or preferably in the form of a 10 to 30 percent by weight aqueous solution, advantageously in an amount of from 2 to 200, in particular from 5 to 50 moles of ammonia per mole of starting material II.

In stage (b), an alkanol, an ether and/or water can be used, examples of suitable ethers being ethyl propyl ether, methyl-tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glykol dimethyl ether, tetrahydrofuran, dioxane, thioanisole and $\beta,\beta'$-dichlorodiethyl ether, and appropriate mixtures of these. It is advantageous to use water or an ether in an amount of from 400 to 10,000 percent by weight, preferably from 500 to 1,000 percent by weight, based on starting material II.

The aminonicotinic acid can be prepared in stage (c) if desired. An alkali metal hydroxide, alkali metal carbonate or alkali metal alcoholate, particularly the sodium or potassium compound, is advantageously used as the alkali metal compound, suitable examples being potassium hydroxide, sodium hydroxide, potassium carbonate, sodium carbonate, lithium hydroxide, lithium carbonate, sodium bicarbonate, potassium bicarbonate, sodium formate, sodium acetate, sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, sodium butylate, sodium isobutylate, sodium sec-butylate, sodium tert.-butylate, sodium ethylene glycolate, sodium propylene-1,2-glycolate, sodium propylene-1,3-glycolate, sodium diethyleneglycolate, sodium triethyleneglycolate, sodium dipropylene-1,2-glycolate, potassium methylate, potassium ethylate, potassium n-propylate, potassium isopropylate, potassium n-butylate, potassium isobutylate, potassium sec-butylate, potassium tert.-butylate, potassium ethyleneglycolate, potassium propylene-1,2-glycolate, potassium diethyleneglycolate, potassium triethyleneglycolate or potassium dipropylene-1,2-glycolate. The reaction is advantageously carried out using a quantity of from 0.5 to 5, preferably from 0.8 to 1.5 equivalents of the alkaline compound per mole of starting material II. In general, water is used as the solvent in stage (c), advantageously in an amount of from 50 to 500, in particular from 100 to 300, percent by weight, based on the total quantity of starting material II.

In general, the reaction is carried out in stage (a) at from 40° to 140° C., in particular from 60° to 120° C., in stage (b) at from 50° to 200° C., in particular from 80° to 180° C., and in stage (c) at from 50° to 150° C., in particular from 80° to 120° C., under atmospheric or under superatmospheric pressure and continuously or batchwise. Additional organic solvents are generally not required.

The reaction can be carried out as follows: a mixture of starting material II, malonitrile and alkanol is kept at the reaction temperature of stage (a) for from 2 to 10 hours. Ammonia and, if appropriate, further alkanol are added and the mixture is kept at the reaction temperature of stage (b) for from 0.5 to 5 hours. If desired, the alkali metal compound and water are then also added, with or without the alkanol having been distilled off, and the mixture is kept at the reaction temperature of stage (c) for from 2 to 8 hours. The end product can be separated off in a conventional manner in stage (b), for example by the addition of organic solvents and filtration of the precipitate, or after stage (c), for example by acidifying the mixture and filtering.

The 2-aminopyridine derivatives obtainable by the process of the invention are valuable starting materials for the preparation of pesticides, drugs, vitamins and dyes. Regarding their use, reference may be made to the above literature and to Ullmanns Encyklopädie der technischen Chemie, volume 8, page 503; volume 14, page 480; and volume 18, pages 195-198. The end products I are starting materials for the pesticides described in German Laid-Open Application DOS No. 2,430,353.

In the examples which follow parts are by weight.

EXAMPLE 1

(a) 100 parts of N,N-(3-chloro-ethoxypropylidene)-N,N-dimethylammonium chloride (obtained from dimethylformamide, phosgene and ethyl vinyl ether), 33 parts of malodinitrile and 450 parts of methanol are refluxed at 68° C. for 6 hours.

(b) The solution is cooled and the solvent is distilled off under reduced pressure. 15 parts of the residue, 80 parts of methanol and 40 parts of liquid ammonia are introduced into a stirred autoclave and heated to 150° C. for 4 hours. After the mixture has been cooled, toluene and ethanol are added until a crystalline residue remains. 6.0 parts (61% of theory) of 2-aminonicotinonitrile of melting point 129°-131° C. are obtained after filtration.

EXAMPLE 2

114 parts of N,N-(3-chloro-3-isobutoxypropylidene)-N,N-dimethylammonium chloride (obtained from dimethylformamide, phosgene and isobutyl vinyl ether) are reacted analogously to Example 1. 5.1 parts (59% of theory) of 2-aminonicotinonitrile of melting point 129° to 131° C. are obtained after filtration.

EXAMPLE 3

The reaction is carried out analogously to Example 1 and after stage (b) (heating in the autoclave) the solvent is distilled off under reduced pressure, 20 parts of water and 3 parts of sodium hydroxide are added to the residue, and the mixture is refluxed for 5 to 6 hours. The mixture is cooled, filtered, acidified with 10% strength by weight hydrochloric acid and cooled again, and the precipitate is filtered off under suction, giving 5.9 parts (52% of theory) of 2-aminonicotinic acid of melting point 305°-310° C.

EXAMPLE 4

The reaction is carried out analogously to Example 2 and after stage (b) (heating in the autoclave) the solvent is distilled off, 15 parts of water and 2.5 parts of sodium hydroxide are added to the residue and the mixture is refluxed for 3-4 hours. The mixture is cooled, filtered, acidified with 10% strength by weight hydrochloric acid and cooled again, and the precipitate is filtered off under suction, giving 5.0 parts (49% of theory) of 2-aminonicotinic acid of melting point 305°-310° C.

EXAMPLE 5

The reaction is carried out analogously to stage (a) of Example 1. After the solution has been cooled, 120 parts of liquid ammonia and 250 parts of methanol are added and the mixture is heated in a stirred autoclave to 150° C. for 6 hours. After the mixture has been cooled, toluene and ethanol are added until a crystalline residue remains. 37 parts (62% of theory) of 2-aminonicotinonitrile of melting point 129°–131° C. are obtained after filtration.

EXAMPLE 6

The reaction is carried out analogously to stage (a) of Example 1. The solution is cooled, and the solvent is distilled off under reduced pressure. 500 parts of 25% strength by weight aqueous ammonia solution is added and the mixture is heated in a stirred autoclave to 150° C. for 8 hours. About 380 parts of solvent are then distilled off, 20 parts of sodium hydroxide are added and the mixture is refluxed for from 4 to 5 hours. The mixture is cooled, filtered, acidified with 10% strength by weight sulfuric acid and cooled again, and the precipitate is filtered off under suction, giving 32 parts (46% of theory) of 2-aminonicotinic acid of melting point 305°–310° C.

We claim:

1. A process for the preparation of 2-aminopyridine derivatives of the formula

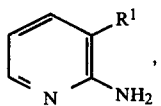

where $R^1$ is cyano or carboxyl, wherein a quaternary ammonium compound of the formula

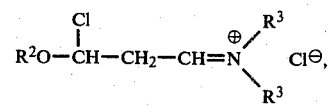

where the individual radicals $R^2$ and $R^3$ can be identical or different and each is an alkyl radical having 1–7 carbon atoms, (a) is reacted with malodinitrile in the presence of an alkanol, (b) the resulting reaction mixture is then reacted with ammonia in the presence of an alkanol, water and/or an ether and, if desired, (c) the aminonicotinonitrile thus obtained is reacted with an alkali metal compound.

2. A process as claimed in claim 1, wherein the reaction is carried using from 0.5 to 3.0 moles of malodinitrile per mole of starting material II.

3. A process as claimed in claim 1, wherein the reaction is carried out using from 1 to 1,000 moles of alkanol per mole of starting material II.

4. A process as claimed in claim 1, wherein the reaction is carried out using from 2 to 200 moles of ammonia per mole of starting material II.

5. A process as claimed in claim 1, wherein the reaction is carried out using water or an ether in an amount from 400 to 10,000 percent by weight, based on starting material II.

6. A process as claimed in claim 1, wherein the reaction is carried out using from 0.5 to 5 equivalents of an alkali compound per mole of starting material II.

7. A process as claimed in claim 1, wherein the reaction in stage (c) is carried out using from 50 to 500 percent by weight of water, based on starting material II.

8. A process as claimed in claim 1, wherein the reaction in stage (a) is carried out at from 40° to 140° C.

9. A process as claimed in claim 1, wherein the reaction in stage (b) is carried out at from 50° to 200° C.

10. A process as claimed in claim 1, wherein the reaction in stage (c) is carried out at from 50° to 150° C.

* * * * *